United States Patent [19] [11] Patent Number: 4,666,455
Jost et al. [45] Date of Patent: May 19, 1987

[54] COMPOSITIONS PIGMENTED WITH N-SUBSTITUTED 1,4-DIKETOPYRROLO-[3,4-C]-PYRROLES

[75] Inventors: Max Jost, Oberwil; Abul Iqbal, Ettingen; Alain C. Rochat, Fribourg, all of Switzerland

[73] Assignee: Ciba-Geigy Corporation, Ardsley, N.Y.

[21] Appl. No.: 823,694

[22] Filed: Jan. 29, 1986

Related U.S. Application Data

[62] Division of Ser. No. 621,649, Jun. 18, 1984, Pat. No. 4,585,878.

[30] Foreign Application Priority Data

Jun. 29, 1983 [CH] Switzerland ............... 3568/83

[51] Int. Cl.$^4$ ................. C07D 487/04; D06P 3/54
[52] U.S. Cl. ................................. 8/506; 8/512; 8/514; 8/513; 8/516; 8/637; 8/922; 8/924; 8/928; 548/453; 548/455
[58] Field of Search ............... 548/453; 8/506, 512, 8/514

[56] References Cited

U.S. PATENT DOCUMENTS

| 4,415,685 | 11/1983 | Iqbal et al. | 524/92 |
| 4,490,542 | 12/1984 | Iqbal et al. | 548/453 |
| 4,579,949 | 4/1986 | Rochat et al. | 546/167 |
| 4,585,878 | 4/1986 | Jost et al. | 548/453 |

FOREIGN PATENT DOCUMENTS 98808 1/1984 European Pat. Off. .

Primary Examiner—A. Lionel Clingman
Attorney, Agent, or Firm—Luther A. R. Hall

[57] ABSTRACT

Compounds of the formula

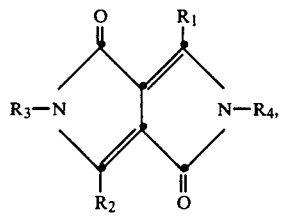

in which $R_1$ and $R_2$ are unsubstituted or substituted phenyl or naphthyl, and $R_3$ and $R_4$ are alkyl, alkoxycarbonyl, phenyl, benzoyl or benszl, are suitable for dyeing high molecular weight organic material.

8 Claims, No Drawings

COMPOSITIONS PIGMENTED WITH N-SUBSTITUTED 1,4-DIKETOPYRROLO-[3,4-C]-PYRROLES

This is a divisional of application Ser. No. 621,649, filed June 18, 1984, now U.S. Pat. No. 4,585,878, issued Apr. 29, 1986.

The invention relates to novel 1,4-diketopyrrolo-[3,4-c]-pyrroles of the formula I

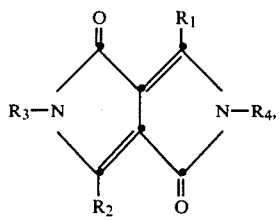

in which $R_1$ and $R_2$ are isocyclic aromatic or heterocyclic aromatic radicals and $R_3$ and $R_4$ independently of one another are substituents which do not confer solubility in water, and $R_3$ or $R_4$ can also be hydrogen.

Formula (I) and the formulae shown below represent only one of the possible tautomeric structures.

An isocyclic aromatic radical $R_1$ or $R_2$ is preferably a mono-, bi-, tri- or tetra-cyclic radical, in particular a mono- or bi-cyclic radical, such as phenyl, diphenyl or naphthyl. A heterocyclic aromatic radical $R_1$ or $R_2$ is preferably a mono-, bi- or tri-cyclic radical. These radicals can be purely heterocyclic or can contain one heterocyclic ring and one or more fused-on benzene rings. Examples of heterocyclic aromatic radicals are pyridyl, pyrimidyl, pyrazinyl, triazinyl, furanyl, pyrrolyl, thiophenyl, quinolyl, cumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isooxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, ortho-sulfobenzimidyl, maleimidyl, naphtharidinyl, benzimidazolonyl, benzoxazolonyl, benzothiazolonyl, benzothiazolinyl, quinazolonyl, pyrimidyl, quinoxalonyl, phthalazonyl, dioxapyrimidinyl, pyridonyl, isoquinolonyl, isoquinolinyl, isothiazolyl, benzisoxazolyl, benzisothiazolyl, indazolonyl, acridinyl, acridonyl, quinazolinedionyl, quinoxalinedionyl, benzoxazinedionyl, benzoxazinonyl and naphthalimidyl. Both the isocyclic and the heterocyclic aromatic radicals can contain the customary substituents which do not confer solubility in water, such as (a) halogen atoms, for example chlorine, bromine or fluorine.

(b) Branched or straight-chain alkyl groups with preferably 1 to 18, in particular 1 to 12, especially 1 to 8 and particularly preferably 1 to 4, C atoms. These alkyl groups can contain substituents which do not confer solubility in water, such as, for example, fluorine, hydroxyl, cyano, —$OCOR_5$, —$OR_6$, —$COOR_5$, —$CON(R_6)(R_7)$ or —$OCONHR_5$, in which $R_5$ is alkyl, aryl, such as naphthyl, or benzyl which is unsubstituted or substituted by halogen, alkyl or —O—alkyl, or a heterocyclic radical and $R_6$ and $R_7$ are hydrogen, alkyl which is unsubstituted or substituted by cyano or hydroxyl, $C_5$-$C_6$-cycloalkyl, aryl or heteroaryl, in particular phenyl which is unsubstituted or substituted by halogen, alkyl or —O—alkyl, or in which $R_6$ and $R_7$, together with the N atom, form a 5-membered or 6-membered hetero ring, for example a morpholine, piperidine or phthalimide ring. Other possible substituents on the alkyl groups are monoalkylated or dialkylated amino groups, aryl radicals, such as naphthyl or, in particular, phenyl which is unsubstituted or substituted by halogen, alkyl or —O—alkyl, or furthermore heterocyclic aromatic radicals, for example the 2-thienyl, 2-benzoxazolyl, 2-benzothiazolyl, 2-benzimidazolyl, 6-benzimidazolonyl, 2-, 3- or 4-pyridyl or 2-, 4- or 6-quinolyl radicals.

If the substituents mentioned under (b) in turn again contain alkyl, this alkyl can be branched or straight-chain and preferably contains 1 to 18, in particular 1 to 12, especially 1 to 8 and particularly preferably 1 to 4, C atoms.

Examples of unsubstituted or substituted alkyl groups are methyl, ethyl, n-propyl, isopropyl, n-butyl, sec.-butyl, tert.-butyl, tert.-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl and benzyl.

(c) The group —$OR_8$, in which $R_8$ is hydrogen, alkyl, aryl, for example naphthyl or, in particular, phenyl which is unsubstituted or substituted by halogen, alkyl or —O—alkyl, $C_5$-$C_6$-cycloalkyl, aralkyl or a heterocyclic radical. Alkyl occurring in the definitions of $R_8$ can have, for example, a number of C atoms mentioned as preferred under (b). Examples of $R_8$ are: methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienyl and pyranylmethyl.

(d) The group —$SR_8$, in which $R_8$ is as defined under (c). Examples of $R_8$ are: methyl, ethyl, n-propyl, isopropyl, phenyl, o-, m- or p-chlorophenyl, o-, m- or p-methylphenyl, α- or β-naphthyl, cyclohexyl, benzyl, thienyl and pyranylmethyl.

(e) The cyano group.

(f) The group of the formula —$N(R_6)(R_7)$, in which $R_6$ and $R_7$ are as defined under (b). Examples are: amino, methylamino, dimethylamino, ethylamino, diethylamino, isopropylamino, β-hydroxyethylamino, β-hydroxypropylamino, N,N-bis(β-hydroxyethyl)-amino, N,N-bis-(β-cyanoethyl)-amino, cyclohexylamino, phenylamino, N-methylphenylamino, benzylamino, dibenzylamino, piperidyl and morpholyl.

(g) The group of the formula —$COOR_5$, in which $R_5$ is as defined under (b). Examples of $R_5$ are: methyl, ethyl, isopropyl, tert.-butyl, n-butyl, phenyl, benzyl and furfuryl.

(h) The group of the formula —$N(R_9)COR_5$, in which $R_5$ is as defined under (b) and $R_9$ is hydrogen, alkyl, aryl, for example naphthyl or, in particular, phenyl which is unsubstituted or substituted by halogen, alkyl or —O—alkyl, $C_5$-$C_6$-cycloalkyl, aralkyl or the radical —$COR_5$, it being possible for two radicals —$COR_5$, together with the N atom, to form a heterocyclic ring. Alkyl occurring in the definitions of $R_9$ can have, for example, a number of C atoms mentioned as preferred under (b). Examples are: acetylamino, propionylamino, utyrylamino, benzoylamino, p-chlorobenzoylamino, p-methylbenzoylamino, N-methylacetylamino, N-methylbenzoylamino, N-succinimido and N-phthalimido.

(i) The group of the formula —N($R_8$)COO$R_5$, in which $R_5$ and $R_8$ are as defined under (b) and, respectively, (c). Examples are the groups —NHCOOCH$_3$, —NHCOOC$_2$H$_5$ or —NHCOOC$_6$H$_5$.

(j) The group of the formula —N($R_8$)CON($R_6$)($R_7$), in which $R_6$, $R_7$ and $R_8$ are as defined under (b) and (c). Examples are: ureido, N-methylureido, N-phenylureido and N,N-2',4'-dimethylphenylureido.

(k) The group of the formula —NHSO$_2$R$_5$, in which $R_5$ is as defined under (b). Examples are: methylsulfonylamino, phenylsulfonylamino, p-toluylsulfonylamino and β-naphthylsulfonylamino.

(l) The groups of the formula —SO$_2$R$_5$ or —SOR$_5$, in which $R_5$ is as defined under (b). Examples are: methylsulfonyl, ethylsulfonyl, phenylsulfonyl, 2-naphthylsulfonyl and phenylsulfoxidyl.

(m) The group of the formula —SO$_2$OR$_5$, in which $R_5$ is as defined under (b). Examples of $R_5$ are: methyl, ethyl, phenyl, o-, m- or p-chlorophenyl, o-, m- or p-methylphenyl and α- or β-naphthyl.

(n) The group of the formula —CON($R_6$)($R_7$), in which $R_6$ and $R_7$ are as defined under (b). Examples are: carbamyl, N-methylcarbamyl, N-ethylcarbamyl, N-phenylcarbamyl, N,N-dimethylcarbamyl, N-methyl-N-phenylcarbamyl, N-α-naphthylcarbamyl and N-piperidylcarbamyl.

(o) The group of the formula —SO$_2$N($R_6$)($R_7$), in which $R_6$ and $R_7$ are as defined under (b). Examples are: sulfamyl, N-methylsulfamyl, N-ethylsulfamyl, N-phenylsulfamyl, N-methyl-N-phenylsulfamyl and N-morpholylsulfamyl.

(p) The group of the formula —N=N—$R_{10}$, in which $R_{10}$ is the radical of a coupling component, or a phenyl radical which is unsubstituted or substituted by halogen, alkyl or —O—alkyl. Alkyl occurring in the definitions of $R_{10}$ can have, for example, a number of C atoms mentioned as preferred under (b). Examples of $R_{10}$ are: the acetoacetarylide, pyrazolyl, pyridonyl, o- or p-hydroxyphenyl, o-hydroxynaphthyl, p-aminophenyl and p-N,N-dimethylaminophenyl radicals.

(q) The group of the formula —OCOR$_5$, in which $R_5$ is as defined under (b). Examples of $R_5$ are: methyl, ethyl, phenyl and o-, m- or p-chlorophenyl.

(r) The group of the formula —OCONHR$_5$, in which $R_5$ is as defined under (b). Examples of $R_5$ are: methyl, ethyl, phenyl and o-, m- or p-chlorophenyl.

Substituents $R_3$ and $R_4$ which do not confer solubility in water can be, in particular:

(1) Branched or straight-chain alkyl groups as defined above under (b).

(2) Branched or straight-chain alkenyl or alkynyl groups with preferably 2 to 18, in particular 2 to 12 and especially 2 to 6, C atoms. These alkenyl and alkynyl groups can in turn carry substituents which do not confer solubility in water, for example as defined under (b). Examples of alkenyl or alkynyl groups are ethylenyl, propylenyl, butenyl, isobutenyl, isoprenyl, 1-pentenyl, 2-methyl-2-butenyl, 3-methyl-1-butenyl, 3-propyl-1-hexenyl, propadienyl, 1,2-butadienyl, ethynyl, propargyl, 1-butynyl and 4-methyl-2-pentynyl.

(3) The group of the formula —COR$_8$, where $R_8$ is as defined under (c).

(4) The group of the formula —CON($R_6$)($R_7$) as defined under (b).

(5) The epoxyethyl group.

(6) Aryl which is unsubstituted or substituted by halogen, such as chlorine or bromine, nitro, cyano, trifluoromethyl, alkyl, —O—alkyl, phenyl, —O—phenyl, alkoxycarbonyl or phenoxycarbonyl, such as phenyl, naphthyl, anthraquinonyl, 4-methylphenyl, 2,4-dichlorophenyl, 4-chlorophenyl, 4-nitrophenyl or 3-methoxyphenyl.

(7) The group of the formula —CR$_{11}$=Y, in which $R_{11}$ is hydrogen, alkyl, or phenyl which is unsubstituted or substituted by chlorine, bromine, nitro, cyano, trifluoromethyl, alkyl, —O—alkyl, phenyl or —O—phenyl and Y is a methine radical derived from an active methylene compound or an imine radical derived from an aromatic or heterocyclic primary amine, in particular from an amine, the amino group of which is on a 5-membered or 6-membered heteroring which contains 1 or 2 nitrogen atoms or 1 nitrogen atom and 1 oxygen or sulfur atom and onto which a benzene nucleus which is unsubstituted or substituted by halogen, alkyl or alkoxy may be fused. A methine radical Y is, for example, a radical of the formula

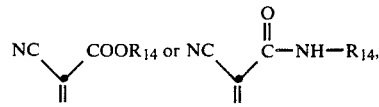

in which $R_{14}$ is $C_1$–$C_8$-alkyl, phenyl, which is unsubstituted or substituted by halogen, such as chlorine, $C_1$–$C_8$-alkyl, $C_1$–$C_8$-alkoxy, nitro or trifluoromethyl, or a radical of the formula

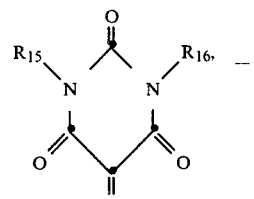

in which $R_{15}$ and $R_{16}$ independently of one another are hydrogen, $C_1$–$C_8$-alkyl or phenyl. An imine radical Y is, for example, the radical of 2-aminopyridine, 2-amino-5-chloropyridine, 2-amino-4-hydroxyquinoline, 5-amino-4,5-dimethylthiazole, 2-aminobenzimidazole or 5-aminobenzimidazolone.

(8) The group of the formula

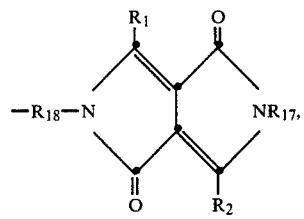

in which $R_1$ and $R_2$ are as defined above, $R_{17}$ is hydrogen or one of the groups defined under (1) to (12) and $R_{18}$ is a divalent radical derived from a $C_1$–$C_8$-dihaloalkane, such as Cl(CH$_2$)$_2$Cl, a diisocyanate, such as toluylene diisocyanate, a $C_1$–$C_{10}$-dicarboxylic acid halide, such as ClCO(CH$_2$)$_4$COCl, an activated ethylene dihalide, such as ClCH$_2$CH=CH—CH$_2$Cl, a phenylene dihalide or a xylylene dihalide. Halogen can be, in particular, chlorine or bromine.

Compounds of the formula I in which $R_1$ and $R_2$ are phenyl or naphthyl and are unsubstituted or carry substituents which do not confer solubility in water, and $R_3$ and $R_4$ are both other than hydrogen and are a substituent which does not confer solubility in water, are of particular interest. In particularly preferred compounds of the formula I, $R_3$ and $R_4$ are the same substituent which does not confer solubility in water.

Preferred compounds are those of the formula I in which $R_1$ and $R_2$ are radicals of the formula

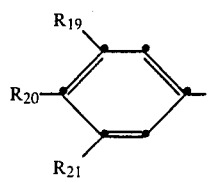
(II)

in which $R_{19}$, $R_{20}$ and $R_{21}$ independently of one another are hydrogen, halogen, carbamyl, cyano, trifluoromethyl, $C_2-C_{13}$-alkylcarbamyl, $C_1-C_{12}$-alkyl, $C_1-C_{12}$-alkoxy, $C_1-C_{12}$-alkylmercapto, $C_2-C_{13}$-alkoxycarbonyl, $C_2-C_{13}$-alkanoylamino, $C_1-C_{12}$-monoalkylamino, $C_2-C_{24}$-dialkylamino, or phenoxy, phenylmercapto, phenoxycarbonyl, phenylcarbamyl or benzoylamino which are unsubstituted or substituted by halogen, $C_1-C_{12}$-alkyl or $C_1-C_{12}$-alkoxy, at least one of the substituents $R_{19}$, $R_{20}$ and $R_{21}$ being hydrogen.

Particularly preferred compounds are those of the formula I in which $R_1$ and $R_2$ are radicals of the formula

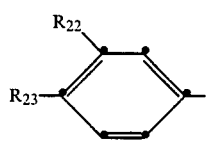
(III)

in which one of the substituents $R_{22}$ and $R_{23}$ is chlorine, bromine, $C_1-C_4$-alkyl, cyano, $C_1-C_4$-alkoxy, phenoxy which is unsubstituted or substituted by chlorine or methyl, carbamyl, $C_2-C_5$-alkylcarbamyl or phenylcarbamyl which is unsubstituted or substituted by chlorine, methyl or methoxy, and the other substituent is hydrogen.

Preferred compounds are those of the formula I in which $R_3$ and $R_4$ are $C_1-C_{12}$-alkyl, $C_2-C_{13}$-alkoxycarbonyl, carbamyl, $C_2-C_{13}$-alkylcarbamyl, $C_2-C_{13}$-alkyl-$C_1-C_4$-alkoxycarbonyl, or phenyl, benzyl or benzoyl which is unsubstituted or substituted by halogen, $C_1-C_{12}$-alkyl, $C_1-C_{12}$-alkoxy, trifluoromethyl or nitro, or the group of the formula

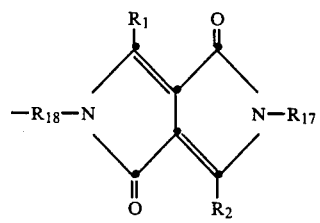

in which $R_1$ and $R_2$ are phenyl or naphthyl and are unsubstituted or carry substituents which do not confer solubility in water, $R_{17}$ is hydrogen and $R_{18}$ is a divalent radical derived from a $C_1-C_8$-dihaloalkane, $C_1-C_{10}$-dicarboxylic acid halide, ethylene dihalide, phenylene dihalide or xylylene dihalide.

Particularly preferred compounds are those of the formula I in which $R_3$ and $R_4$ are $C_1-C_8$-alkyl, $C_2-C_5$-alkoxycarbonyl, carbamyl, $C_2-C_{13}$-alkyl-$C_1-C_4$-alkoxycarbonyl, or phenyl which is unsubstituted or substituted by chlorine, bromine, $C_1-C_4$-alkyl, $C_1-C_4$-alkoxy, trifluoromethyl or nitro.

Compounds of the formula I in which $R_1$ and $R_2$ are radicals of the formula

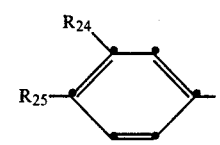
(IV)

in which one of the substituents $R_{24}$ and $R_{25}$ is $C_1-C_4$-alkyl and the other is hydrogen, and $R_3$ and $R_4$ are $C_1-C_8$-alkyl, are of particular interest.

Compounds of the formula I in which $R_1$ and $R_2$ are radicals of the formula

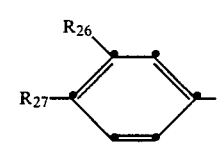
(V)

in which one of the substituents $R_{26}$ and $R_{27}$ is cyano and the other is hydrogen, and $R_3$ and $R_4$ are $C_1-C_4$-alkyl are of further interest.

The compounds of the formula I can be prepared in various ways, for example (a) by reacting the compound of the formula

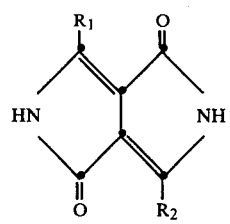
(VI)

with a compound containing the radicals $R_3$ and/or $R_4$ as leaving groups, in an organic solvent, or (b) by reacting 2 moles of a compound of the formula

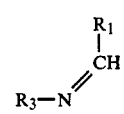
(VII)

or

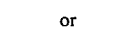
(VIII)

or one mole each of the compounds of the formulae (VII) and (VIII), with 1 mole of a succinic acid diester in the presence of a base and an organic solvent (cf. J. Chem. Soc. 1976, page 5) and then dehydrogenating the product.

The starting compounds of the formulae (VI), (VII) and (VIII) are known and can be prepared by known processes.

Depending on the nature of their substituents and on the polymer to be dyed, the compounds of the formula I can be used, in particular, as polymer-soluble dyes for, for example, polystyrene, polyamides, ABS and, in particular, for linear polyesters, and also as pigments for high molecular weight organic material. Examples of linear polyesters are in particular those which are obtained by polycondensation of terephthalic acid or esters thereof with glycols of the formula HO—($CH_2$)$_n$—OH, in which n is a number from 2 to 10, or with 1,4-di-(hydroxymethyl)-cyclohexane, or by polycondensation of glycol ethers of hydroxybenzoic acids, for example p-($\beta$-hydroxyethoxy)-benzoic acid. The term linear polyesters also includes copolyesters which are obtained by replacing some of the terephthalic acid by another dicarboxylic acid and/or replacing some of the glycol by another diol.

However, the polyethyleneterephthalates are of particular interest.

The linear polyesters to be dyed are advantageously mixed intimately with the dye in the form of a powder, chips or granules. This mixing can be effected, for example, by coating the polyester particles with the finely divided dry dye powder or by treating the polyester particles with a solution or dispersion of the dye in an organic solvent and then removing the solvent.

The substance to be dyed can also be dyed by the bath-dyeing method.

Mixtures of the compounds of the formula I and mixtures of one or more compounds of the formula I with disperse dyes can be used to adjust the shade.

Finally, the compound of the formula I can also be added directly to the molten polyester or before or during polycondensation of the polyethylene terephthalate.

The ratio of dye to polyester can vary within wide limits, depending on the desired depth of shade. In general, it is advisable to use 0.01–3 parts of dye per 100 parts of polyester.

The polyester particles thus treated are melted in an extruder by known processes and are pressed to articles, in particular films or fibres, or cast to sheets.

When used as pigments, it is advantageous to convert the products obtained in the synthesis into a finely disperse form. This can be effected in various ways, for example:

(a) by grinding or kneading, advantageously in the presence of grinding assistants, such as inorganic or organic salts, with or without the addition of organic solvents. After the grinding, the assistants are removed in the customary manner, for example soluble inorganic salts are removed with water and water-insoluble organic solvents are removed by, for example, steam distillation;

(b) by reprecipitation from sulfuric acid, methanesulfonic acid, trichloroacetic acid or polyphosphoric acid;

(c) in the case of products in which $R_3$ or $R_4$ is hydrogen, by conversion of the crude pigment into an alkali metal salt or amine salt and hydrolysis of the latter. This is effected, for example, by stirring the crude pigment with a base, for example with an alkali metal hydroxide or alcoholate, ammonia or an amine, in a polar organic solvent, such as dimethylformamide, whereupon all or some of the pigments dissolve. The pigment is precipitated by hydrolysis, preferably by acidification of the solution, which may be filtered.

It may prove advantageous to after-treat the pigments treated according to (a), (b) or (c) with organic solvents, preferably with those which have boiling points above 100° C.

Solvents which prove to be particularly suitable are benzenes which are substituted by halogen atoms or alkyl or nitro groups, such as the xylenes, chlorobenzene, o-dichlorobenzene or nitrobenzene, and pyridine bases, such as pyridine, picoline or quinoline, and furthermore ketones, such as cyclohexanone, ethers, such as ethylene glycol monomethyl or monoethyl ether, amides, such as dimethylformamide or N-methyl-pyrrolidone, and dimethylsulfoxide, sulfolane or water by itself, if necessary under pressure. The after-treatment can also be carried out in water in the presence of organic solvents and/or with the addition of surface-active substances, or aliphatic amines or with liquid ammonia.

Depending on the intended use, it proves to be advantageous to use the pigments as toners or in the form of preparations.

The high molecular weight organic material can be of natural or synthetic origin. It can be, for example, a natural resin or a drying oil, rubber or casein or a modified natural substance, such as chlorinated rubber, oil-modified alkyd resins or viscose, a cellulose ether or ester, such as cellulose acetate, cellulose propionate, cellulose acetobutyrate or nitrocellulose, or, in particular, a man-made synthetic organic polymer (duroplast or thermoplast), such as those obtained by polymerisation, polycondensation or polyaddition. Polymerisation resins are, in particular, polyolefines, such as polyethylene, polypropylene or polyisobutylene, and furthermore substituted polyolefines, such as polymers of vinyl chloride, vinyl acetate, styrene, acrylonitrile, acrylates and/or methacrylates or butadiene, and copolymers of the monomers mentioned, in particular ABS or EVA.

Polyaddition and polycondensation resins are the condensation products of formaldehyde with phenols, the so-called phenoplasts, and the codensation products of formaldehyde with urea, thiourea and melamine, the so-called aminoplasts, the polyesters used as surface-coating resins, and in particular both those which are saturated, for example alkyd resins, and those which are unsaturated, for example maleate resins, and furthermore linear polyesters and polyamides or silicones.

The high molecular weight compounds mentioned can be used by themselves or in mixtures, as plastic compositions or melts, which may, if appropriate, be spun to fibres.

They can also be in the form of their monomers or in the polymerised state in dissolved form as film-forming agents or binders for varnishes or printing inks, for example linseed oil varnish, nitrocellulose, alkyd resins, melamine resins and urea/formaldehyde resins or acrylic resins.

The high molecular weight organic substances are pigmented with the pigments of the formula (I), for example, by mixing such a pigment, if appropriate in the form of a masterbatch, with these substrates using roll mills or mixing or grinding apparatuses. The pigmented material is then brought into the desired final form by processes which are known per se, such as calendering, pressing, extrusion, brushing, casting or injectionmoulding. It is frequently desirable to incorporate so-called plasticisers into the high molecular weight compounds before shaping in order to produce non-rigid shaped articles or to reduce their brittleness. Examples of suitable plasticisers are esters of phosphoric acid, phthalic acid or sebacic acid. In the process according to the invention, the plasticisers can be incorporated into the polymers before or after incorporation of the pigment. It is furthermore possible also to add fillers or other colouring constituents, such as white, coloured or black pigments, in any amounts, besides the compounds of the formula (I), to the high molecular weight organic substances for the purpose of achieving various colour shades.

For pigmenting varnishes and printing inks, the high molecular weight organic materials and the compounds of the formula (I) are finely dispersed or dissolved in a common organic solvent or solvent mixture, if necessary together with additives, such as fillers, other pigments, siccatives or plasticisers. A procedure may be followed here in which the individual components are dispersed or dissolved by themselves, or several of them are dispersed or dissolved together, and only then are all the components brought together.

The resulting dyeings, for example in plastics, fibres, varnishes or prints, are distinguished by a yellow to red colour shade, a very good depth of shade, high saturation, good dispersibility, good fastness to overlacquering, migration, heat, light and weathering and a high gloss and good IR reflectance properties.

The compounds of the formula (I) can also be used as photoelectrophoretic toners.

When the compounds of the formula (I) are present as a solution in the polymers used, they are also distinguished by a pure colour shade, a good depth of shade, good fastness properties, in particular fastness to light and sublimation, and also by high fluorescence. They are suitable for use in solar energy collectors and for the production of laser beams.

In the examples which follow, parts and percentages are by weight, unless indicated otherwise.

EXAMPLE 1a 14.5 Parts of 1,4-diketo-3,6-diphenylpyrrolo-[3,4-c]-pyrrole, 15 parts of anhydrous potassium carbonate, 40 parts of methyl p-toluenesulfonate and 170 parts of dry nitrobenzene are heated at 200°–205° C. for one hour, with stirring. After cooling to 20° C., the 1,4-diketo-2,5-dimethyl-3,6-diphenylpyrrolo-[3,4-c]-pyrrole obtained is filtered off, washed with toluene, then methanol and thereafter with hot water and dried. 10.85 parts of orange crystals of the compound of the formula (IX) are obtained (melting point 236°–238° C.).

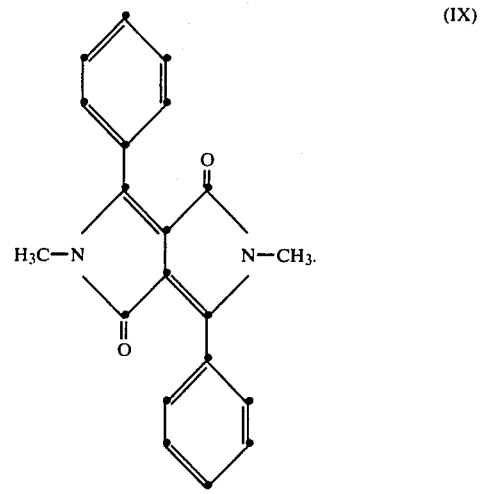

EXAMPLE 1b

1 Part of the dye obtained according to Example 1a is ground under wet conditions with 2 parts of a 50% aqueous solution of the sodium salt of dinaphthylmethanedisulfonic acid and the mixture is dried.

0.1 part of this dye product is stirred with 0.1 part of sodium oleyl-methyl-tauride, 0.1 part of sodium dinaphthylmethanedisulfonate and 0.5 part of ammonium sulfate. 200 parts of a dyebath are prepared therefrom by dilution with water, and the pH is brought to 5 with 85% aqueous formic acid. 10 parts of a diolene fabric (polyester) are introduced into this bath at 50° C. and the temperature is increased to 120° C. in the closed vessel in the course of 30 minutes and then to 130° C. in the course of a further 10 minutes. The fabric is then rinsed thoroughly. A strong yellow dyeing is obtained, the dye being exhausted very well from the dyebath.

EXAMPLE 2

6.8 Parts of 1,4-diketo-3,6-di-(3'-cyanophenyl)pyrrolo-[3,4-c]-pyrrole, 6 parts of anhydrous potassium carbonate and 16 parts of methyl p-toluenesulfonate are heated at 200°–205° C. in 100 parts of dry nitrobenzene for 2 hours, with stirring. After the suspension has been cooled, the dye formed is filtered off and washed with nitrobenzene, acetone and finally with hot water. After drying, 5.5 parts of 1,4-diketo-2,5-dimethyl-3,6-di-(3'-cyanophenyl)-pyrrolo-[3,4-c]-pyrrole [formula (X)] are obtained in the form of brown-red crystals. After being finely divided, the dye gives red shades in PVC and varnishes, with good fastness to light and migration.

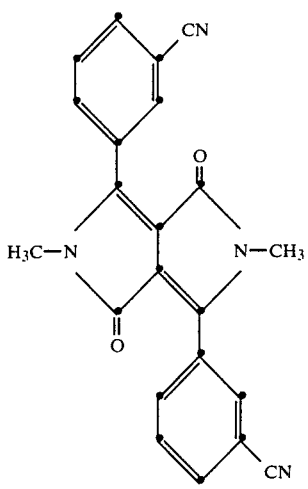

(X)

EXAMPLE 3

The procedure described in Example 2 is repeated, using 6.8 parts of 1,4-diketo-3,6-di-(4'-cyanophenyl)pyrrolo-[3,4-c]-pyrrole instead of 6.8 parts of 1,4-diketo-3,6-di-(3'-cyanophenyl)-pyrrolo-[3,4-c]-pyrrole. 5.5 parts of the compound of the formula XI

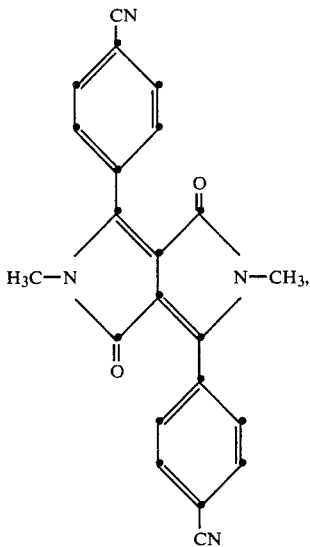

(XI)

which dyes PVC and varnishes in brown-orange shades of good fastness to light and migration, are obtained.

EXAMPLE 4

(4a) A solution of 16 parts of methyl toluene-4-sulfonate in 30 parts of dimethylformamide is added dropwise to a suspension of 7.2 parts of 1,4-diketo-3,6-di-(3'-chlorophenyl)-pyrrolo-[3,4-c]-pyrrole and 11.1 parts of potassium carbonate in 70 parts of dimethylformamide at 135° C. in the course of 40 minutes, with stirring. The mixture is subsequently stirred at 135°–140° C. for 10 minutes, and is then cooled to 20° C. and filtered. The product filtered off is washed twice with a little dimethylformamide and then with methanol and with hot water at 90° C. The crude product is suspended in water and the suspension is heated to the boiling point and filtered. To remove unreacted starting material, the dried, powdered crude product is heated at the boiling point with 175 parts of toluene and, after cooling to 15° C., 400 parts of petroleum ether (boiling point 40°–60° C.) are added to the filtered solution. The 1,4-diketo-2,5-dimethyl-3,6-di-(3'-chlorophenyl)-pyrrolo-[3,4-c]-pyrrole (formula XII) precipitated is filtered off and dried. It is an orange-red powder with a melting point of 226°–227° C. A yellow solution in dimethylformamide shows marked yellow fluorescence. The dye gives pure yellow shades of good fastness to light and sublimation on PES by the method described in Example 1b.

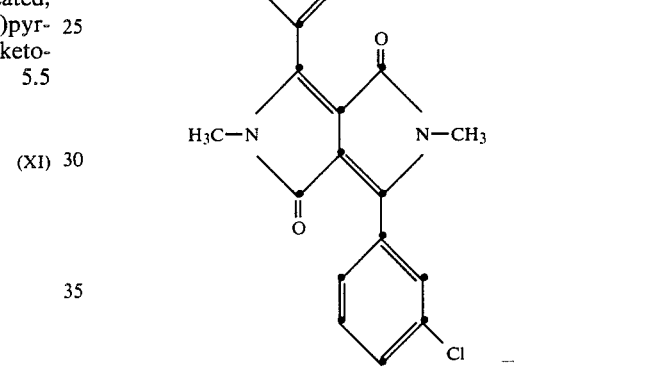

(XII)

(4b) The methyl toluene-4-sulfonate is replaced by ethyl toluene-4-sulfonate. 1,4-Diketo-2,5-diethyl-3,6-di-(3'-chlorophenyl)-pyrrolo-[3,4-c]-pyrrole is obtained in the form of a yellow powder of melting point 203°–205° C. and with similar properties.

EXAMPLE 5

9.5 Parts of 1,4-diketo-3,6-di-(3'-methylphenyl)pyrrolo-[3,4-c]pyrrole, 9 parts of anhydrous potassium carbonate and 24 parts of methyl p-toluenesulfonate are heated at 190° C. with 85 parts of nitrobenzene for 1 hour, with stirring. The cooled reaction mixture is filtered. The dye formed remains dissolved in the solvent. The nitrobenzene is removed by means of steam distillation and the crude dye is purified by crystallisation from 45 parts of toluene. 3.8 parts of 1,4-diketo-2,5-dimethyl-3,6-di-(3'-methylphenyl)pyrrolo-[3,4-c]-pyrrole are obtained in the form of orange crystals of melting point 195°–197° C. (formula XIII). The dye gives a pure yellow shade of good fastness properties on PES by the method described in Example 1b.

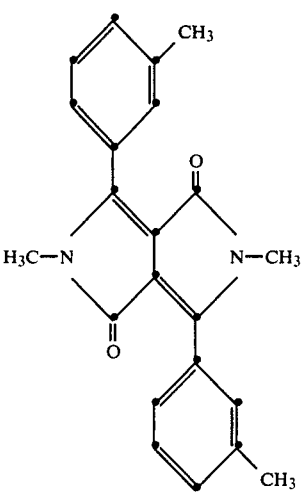
(XIII)

EXAMPLE 6

9.5 Parts of 1,4-diketo-3,6-di-(4'-methylphenyl)pyrrolo-[3,4-c]-pyrrole, 9 parts of anhydrous potassium carbonate, 24 parts of methyl p-toluenesulfonate and 110 parts of nitrobenzene are stirred at 200° C. for ½ hour. After the mixture has been cooled, the dye is filtered off and washed with a little nitrobenzene and then with methanol and hot water. After drying, 5.8 parts of 1,4-diketo-2,5-dimethyl-3,6-di-(4'-methylphenyl)-pyrrolo-[3,4-c]-pyrrole are obtained in the form of yellowish-tinged red crystals of melting point 260° C. (formula XIV). The dye gives pure yellow shades of good fastness properties on PES by the method described in Example 1.

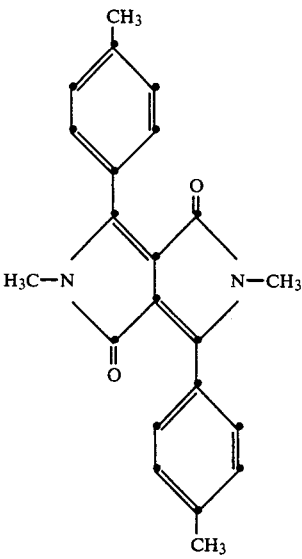
(XIV)

EXAMPLE 7

8.1 Parts of a 30% methanolic solution of sodium methylate are added to a suspension of 5.8 parts of 1,4-diketo-3,6-diphenylpyrrolo-[3,4-c]-pyrrole in 60 parts of dimethylformamide at 20° C., with stirring. The mixture is stirred at 25° C. for 20 minutes. 15 parts of solvent are distilled off under 20 mbar, the mixture is cooled to 20° C., 8.4 parts of n-butyl bromide are added and the mixture is stirred at 60° C. for 20 hours and then at 100° C. for 2 hours. When the reaction has ended, the mixture is poured onto 500 parts of water, heated to the boiling point and then cooled to 10° C. The crude product filtered off is heated to the boiling point with 100 parts of methanol. The mixture is filtered hot and the undissolved portion and the filtrate are worked up separately.

The undissolved portion can be crystallized from a copious amount of methanol. The resulting product is 1,4-diketo-2-n-butyl-3,6-diphenylpyrrolo-[3,4-c]-pyrrole of melting point 250°-252° C. (formula XV). This dye has a very good affinity to PES and gives a strong yellow dyeing with very good fastness to sublimation and adequate fastness to light by the method described in Example 1b.

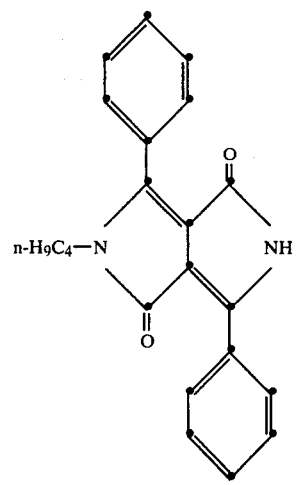
(XV)

The product isolated from the cooled filtrate is crystallised again from cyclohexane. The resulting 1,4-diketo-2,5-di-n-butyl-3,6-diphenylpyrrolo-[3,4-c]-pyrrole of melting point 123°-124° C. (formula XVI) gives a pure yellow shade of very good fastness to sublimation and good fastness to light on PES by the dyeing method described in Example 1b.

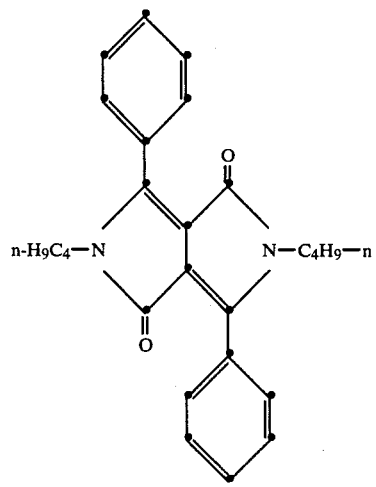
(XVI)

EXAMPLE 8

5.6 Parts of potassium t-butylate are added to a suspension of 5.8 parts of 1,4-diketo-3,6-diphenylpyrrolo-[3,4-c]-pyrrole in 70 parts of dimethylformamide at 20° C. and the mixture is stirred at 20° C. for 1 hours. 7.6 parts of benzyl chloride are then added to the mixture and the mixture is kept at 65° C. for 2 hours. After cooling to 20° C., the reaction product is filtered off and washed with a little dimethylformamide and then with acetone and hot water. After drying, 4.5 parts of 1,4-diketo-2,5-dibenzyl-3,6-diphenylpyrrolo-[3,4-c]-pyrrole (formula XVII) are obtained and, if necessary, can be crystallised from dimethylformamide. Yellow-orange crystals of melting point 290°-292° C. are formed.

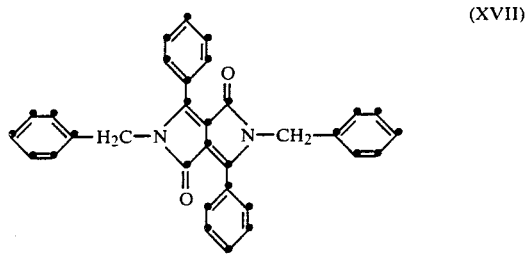

(XVII)

EXAMPLE 9

5.8 Parts of 1,4-diketo-3,6-diphenylpyrrolo-[3,4-c]-pyrrole are stirred with 50 parts of benzoyl chloride at 190° C. for 22 hours. The starting material dissolves in the course of the reaction. On cooling of the reaction mixture, most of the reaction product precipitates. The reaction mixture is introduced into 320 parts of methanol, with stirring, and the mixture is stirred for 2 hours, without heating. The precipitated product is filtered off, washed with methanol and dried. 4.9 parts of ochre-coloured crude product which is purified by crystallisation from 50 parts of dimethylformamide, with addition of a filtration assistant, are obtained. 3.8 parts of 1,4-diketo-2,5-dibenzoyl-3,6-diphenylpyrrolo-[3,4-c]-pyrrole are obtained in the form of brownish-yellow crystals (formula XVIII).

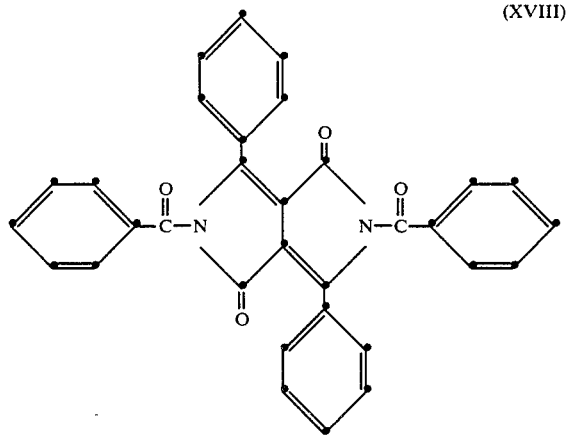

(XVIII)

EXAMPLE 10

(a) 0.5 part of potassium t-butylate is added to a mixture of 8.7 parts of diethylsuccinate, 25 parts of 4,4'-dichlorobenzylaniline and 60 parts of dry dimethylformamide at −17° C. under a nitrogen atmosphere. The temperature increases to −11° C. After the mixture has been stirred for 15 minutes, a further 0.5 part of potassium t-butylate is added at −16° C. and the mixture is then stirred at −10° to −15° C. for 2 hours. After about 25 minutes, a light yellow solution is formed from the original suspension.

After addition of 3 parts of glacial acetic acid, mixed with 15 parts of ethanol, the mixture is stirred into 1,000 parts of water. After the mixture has been stirred for half an hour, the precipitate is filtered off and dried at 70° C. in vacuo. The resulting 26 parts of a product mixture are stirred with 420 parts of methanol at the boiling point for 2 hours. The suspension is cooled and the precipitate is filtered off, washed with methanol and dried at 70° C. in vacuo.

The pre-purified product (16 parts) is stirred with 250 parts of n-butanol at the boiling point for 10 minutes. The suspension is allowed to cool to 80° C., the undissolved product II (see below) is then filtered off, the filtrate is cooled to 20° C. and, after 1 hour, the product I which has crystallised out is filtered off. After washing with methanol and drying, 4.6 parts of the colourless product I of melting point 257°-258° C. are obtained. Crystallisation from n-butanol gives the pure product of melting point 259°-260° C. According to the analysis and the mass spectrum (M+ 580) and the NMR spectrum, the product has the formula:

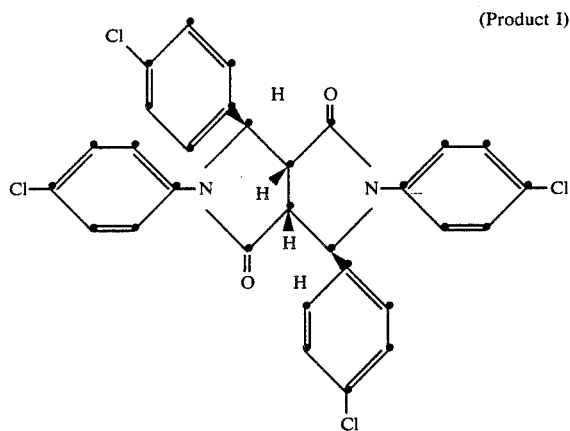

(Product I)

(b) 1.45 parts of product I, 1.7 parts of 2,3-dichloro-5,6-dicyanobenzoquinone (DDQ) and 40 parts of o-dichlorobenzene are stirred at the boiling point for 15 hours, and then, after addition of 1.7 parts of DDQ, the mixture is kept at the boiling point for a further 15 hours. Thereafter, the reaction mixture is freed from the o-dichlorobenzene by means of steam distillation, with the addition of 40 parts of 30% sodium hydroxide solution and 15 parts of dithionite. The suspension which remains is filtered off and the precipitate is washed neutral with water and dried. The crude product (1 part) is dissolved in 70 parts of chlorobenzene at the boiling point and, after addition of a filtration assistant, the solution is filtered. The solution is concentrated to about ¼ of the original volume under reduced pressure. The crystals filtered off after the mixture has been left to stand for 15 hours are washed with methanol and stirred with 25 parts of n-butanol at the boiling point for 10 minutes. The product, which is sparingly soluble in n-butanol, is filtered off, washed with n-butanol and methanol and dried. 0.44 part of 1,4-diketo-2,5-di-(4'-chlorophenyl)-3,6-di-(4''-chlorophenyl)-pyrrolo-[3,4-c]-pyrrole are obtained in the form of yellow crystals which have a melting point above 300° C. (formula XIX).

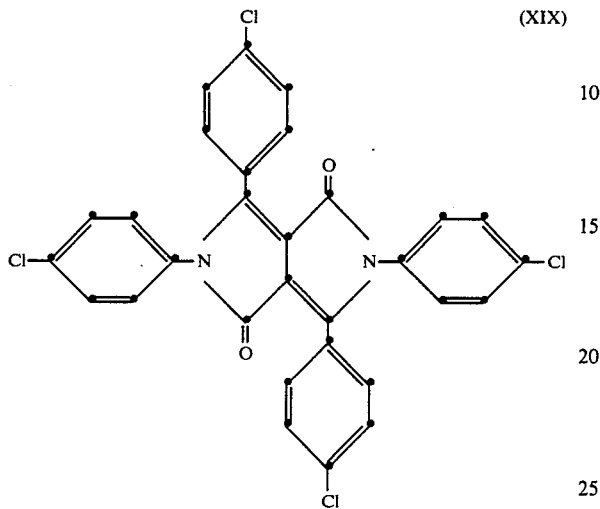
(XIX)

(c) After crystallisation from chlorobenzene, product II has a melting point of 322°–325° C. According to analysis and the mass spectrum (M+ 829), the following formula can be attributed to it:

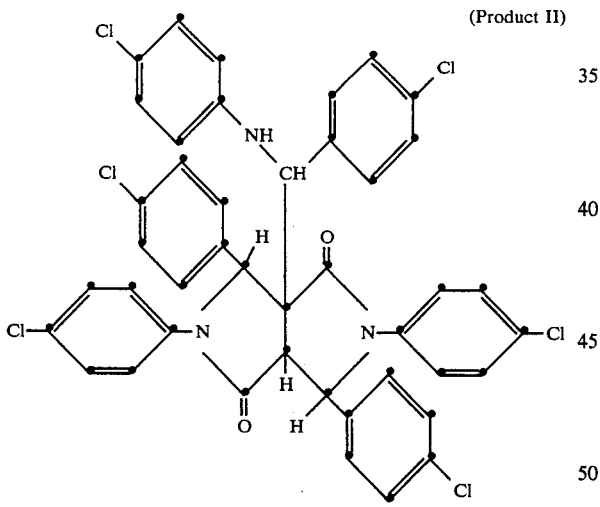
(Product II)

EXAMPLE 11

11.6 Parts of 1,4-diketo-3,6-diphenylpyrrolo-[3,4-c]-pyrrole and 22 parts of potassium carbonate are suspended in 80 parts of dimethylformamide. The mixture is heated at 128° C., and a mixture of 20 parts of allyl bromide and 30 parts of dimethylformamide is added in the course of 25 minutes. During the addition, the temperature falls to 122° C. The reaction mixture is subsequently stirred at about 124° C. for 20 minutes and finally at 20° C. for 2 hours. The reaction product precipitated is filtered off and washed twice with a little dimethylformamide and then with methanol and finally with hot water at 90° C. After drying, 10.5 parts of 1,4-diketo-2,5-diallyl-3,6-diphenylpyrrolo-[3,4-c]-pyrrole of the formula below are obtained in the form of reddish-tinged yellow ctystals of melting point 216°–217° C. and M+ 368.

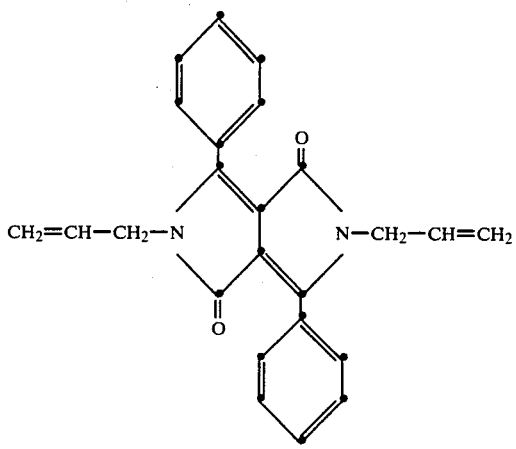

EXAMPLE 12

A mixture of 9.8 parts of ethyl chloroacetate and 20 parts of dimethylformamide is added to a mixture, warmed to 145° C., of 5.8 parts of 1,4-diketo-3,6-diphenylpyrrolo-[3,4-c]-pyrrole, 8.5 parts of sodium carbonate and 60 parts of dimethylformamide in the course of 30 minutes. The brown-yellow solution formed is subsequently stirred at 140°–145° C. for 30 minutes, cooled and poured onto 1,000 parts of water of 15° C. After the mixture has been left to stand at 20° C. for one hour, the aqueous phase is poured off and the crude product is heated to the boiling point with 200 parts of ethanol. The suspension formed is filtered at 20° C. and the product is washed with ethanol and then with water of 90° C. and dried. 5.6 parts of a yellow product of melting point 204°–208° C. are obtained. Pure 1,4-diketo-2,5-di-(carboethoxymethyl)-3,6-diphenylpyrrolo-[3,4-c]-pyrrole of the following formula of melting point 209°–210° C. and M+ 460 is obtained by crystallisation from toluene.

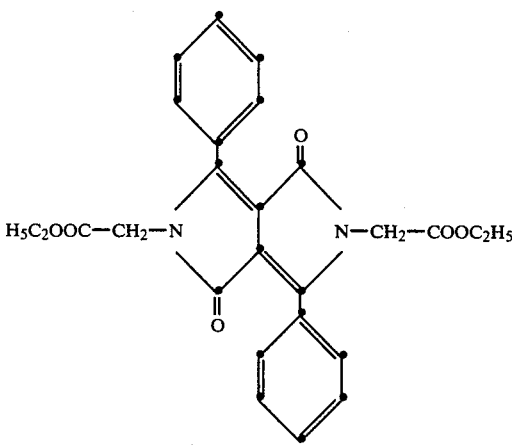

EXAMPLE 13

5.8 Parts of 1,4-diketo-3,6-diphenylpyrrolo-[3,4-c]-pyrrole are suspended in 270 parts of anhydrous dimethylformamide, and 8 parts of 30% sodium methylate solution are added, with stirring. The mixture is stirred at 70°–75° C. for 2 hours and the violet solution is then cooled to 20° C. 30 parts of dimethylformamide are distilled off at about 45° C. under a pressure of 20 mbar. After aeration, 4.6 parts of chloroacetonitrile are added and the mixture is stirred at 85°–90° C. for 10 hours. The brown-yellow, somewhat cloudy solution is then concentrated to 1/5 of the original volume under reduced pressure. The solution which remains is stirred into 500 parts of water and the suspension is stirred for 1 hour. The precipitate is filtered off, washed with water and dried. For pre-purification, the powdered product is stirred with 80 parts of methanol at the boiling point for 1 hour. The product is filtered off, washed with methanol and dried and stirred with 100 parts of glacial acetic acid at the boiling point for 1 hour. The suspension is filtered hot; the filtrate and product are worked up separately.

The glacial acetic acid filtrate is concentrated to a small volume and the concentrate is cooled. The precipitate which has separated out is filtered off and recrystallised twice from a little dimethylformamide. According to analysis, the purified yellow product, which has a melting point above 300° C., has the formula:

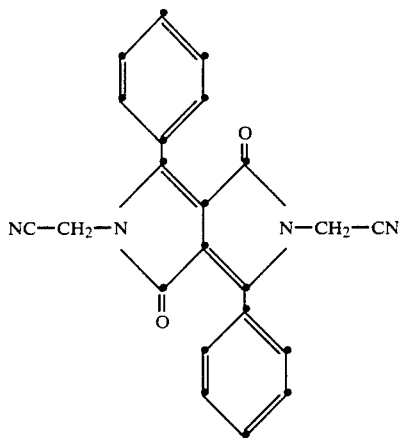

[1,4-Diketo-2,5-di-(cyanomethyl)-3,6-diphenylpyrrolo-[3,4-c]-pyrrole].

The content which is insoluble in glacial acetic acid is stirred with 70 parts of dimethylformamide at the boiling point for 1 hour and the undissolved, unreacted starting material (2 parts) is filtered off at 100° C. The filtrate is evaporated to dryness under reduced pressure. The residue is dissolved in 520 parts of o-dichlorobenzene at the boiling point. A small undissolved portion is filtered off and the solution is left to cool. 0.35 part of a product to which, according to analysis, is attributed the following formula

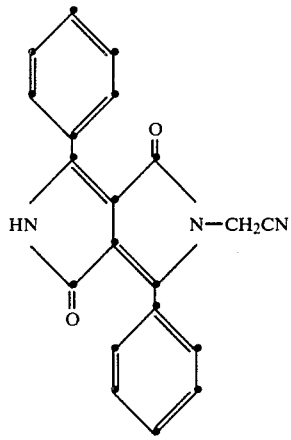

[1,4-Diketo-2-cyanomethyl-3,6-diphenylpyrrolo-[3,4-c]-pyrrole]

is obtained. The dyestuff gives yellow shades on PES by the method described in Example 1b; its melting point is above 310° C.

EXAMPLE 14

4.0 Parts of α,α-dichloro-m-xylene, dissolved in 20 parts of dimethylformamide, are added dropwise to a suspension of 5.8 parts of 1,4-diketo-3,6-diphenylpyrrolo-[3,4-c]-pyrrole and 8.5 parts of sodium carbonate in 100 parts of dimethylformamide at 140°–142° C. in the course of 40 minutes, with stirring. After the mixture has been stirred at 140°–142° C. for 4 hours, it is cooled. The product filtered off and the filtrate are worked up separately.

The product filtered off is washed with hot water and dried. After crystallization from dimethylformamide, a small amount of a yellow product is obtained, to which, according to analysis, the following structure is attributed:

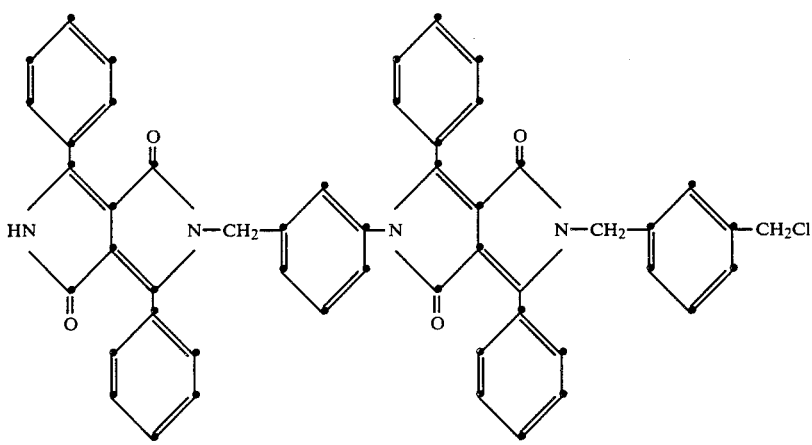

Element analysis:

Calculated for $C_{52}H_{37}ClN_4O_4$ (in %): C 76.41, H 4.56, N 6.86%; Found (in %): C 75.4, H 4.7, N 7.0%.

The filtrate obtained above is left to stand for 20 hours, a small amount of precipitated starting material is filtered off and the filtrate is evaporated to dryness in vacuo. The residue is taken up in methanol and filtered off and the resulting yellow product is washed with methanol. After comminution, it is washed with methanol and water and finally dried in vacuo at 70° C. The resulting product is a mixture. It sinters at 190° C. and melts from 210° C., with gradual decomposition.

A product to which, according to analysis, the following formula is attributed:

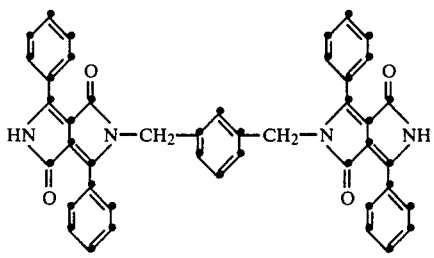

can be isolated by crystallisation from a little dimethylformamide.

Elemental analysis: Calculated for $C_{44}H_{30}N_4O_4$ (in %): C 77.86, H, 4.46, N, 8.26%; Found (in %): C 77.1, H 4.8, N 7.8%.

EXAMPLE 15

A solution of 16 parts of ethyl toluene-4-sulfonate in 15 parts of dimethylformamide is added to a mixture, warmed to 140°-142° C., of 5.8 parts of 1,4-diketo-3,6-diphenylpyrrolo-[3,4-c]-pyrrole, 12.2 parts of potassium carbonate and 60 parts of dimethylformamide in the course of 30 minutes, with stirring. The brown-yellow solution formed is subsequently stirred at 142° C. for 5 minutes, and 100 parts of methanol are added at 70° C. The yellow precipitate which has separated out is filtered off at 15° C., washed with methanol and with hot water at 90° C. and dried. The crude product (3.6 parts) is recrystallised first from 40 part of dimethylformamide and then from 100 parts of n-butanol. 2.8 parts of 1,4-diketo-2,5-diethyl-3,6-diphenylpyrrolo-[3,4-c]-pyrrole of the following formula are obtained in the form of orange-yellow needles of melting point 229°-230° C.:

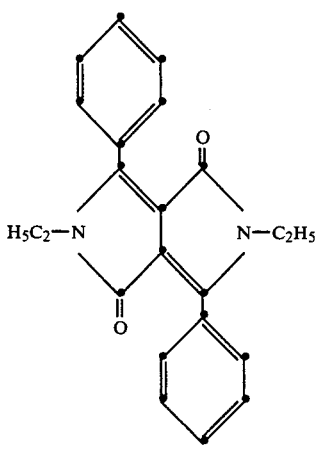

EXAMPLE 16

A solution of 11.2 parts of methyl toluene-4-sulfonate in 20 parts of dimethylformamide is added to a suspension of 7.2 parts of 1,4-diketo-3,6-di-(4'-chlorophenyl)-pyrrolo-[3,4-c]-pyrrole and 11.2 parts of potassium carbonate in 80 parts of dimethylformamide at 143° C. in the course of 25 minutes, with stirring. After the mixture has been stirred at 142°-145° C. for a further 30 minutes, another solution of 6 parts of methyl toluene-4-sulfonate in 10 parts of dimethylformamide is added in the course of 10 minutes. The resulting reaction mixture is kept at 142°-145° C. for a further 20 minutes and, finally, is cooled to 20° C. The precipitate is filtered off, rinsed twice with a little dimethylformamide and then with ethanol and hot water at 90° C. and dried. The crude product (3.4 parts) is dissolved in 550 parts of chlorobenzene at the boiling point. The solution is clarified by filtration and the purified product crystallises out. After the mixture has been left to stand at 20° C. for several hours, the 1,4-diketo-2,5-dimethyl-3,6-di-(4'-chlorophenyl)-pyrrolo-[3,4-c]-pyrrole is separated off. 3 parts of orange crystals of melting point 337°-339° C. of the following formula

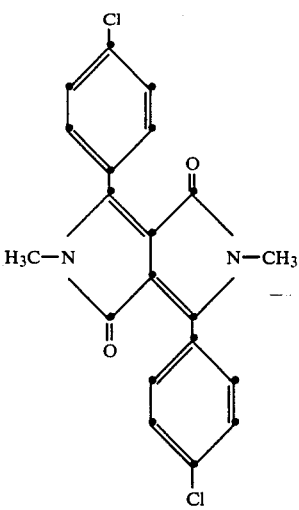

are obtained.

EXAMPLE 17

7.2 Parts of 1,4-diketo-3,6-di-(4'-chlorophenyl)-pyrrolo-[3,4-c]-pyrrole and 11.2 parts of potassium carbonate are suspended in 80 parts of dimethylformamide, with stirring. The mixture is warmed to 141° C. and a solution of 16 parts of ethyl toluene-4-sulfonate in 20 parts of dimethylformamide is added in the course of 45 minutes. The mixture is subsequently stirred at 145° C. for 30 minutes and is finally cooled to 20° C. The precipitate which has been filtered off is washed first with a little dimethylformamide and then with methanol and with hot water at 90° C. and dried. The powdered crude product is stirred with 200 parts of n-butanol at the boiling point for 2 hours. The precipitate containing the starting material is filtered off. 1 part of orange-yellow crystals separates out from the filtrate, on cooling. The 1,4-diketo-2,5-diethyl-3,6-di-(4'-chlorophenyl)-pyrrolo-[3,4-c]-pyrrole of the following formula has a melting point of 276°-277° C.

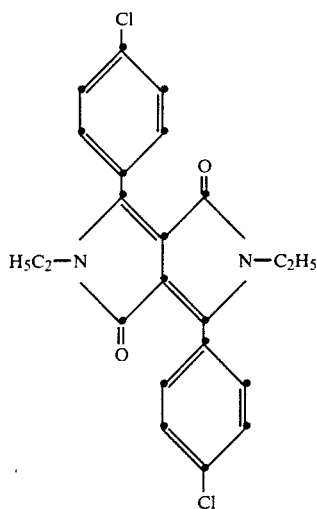

EXAMPLE 18

7.2 Parts of 1,4-diketo-3,6-di-(4'-chlorophenyl)-pyrrolo-[3,4-c]-pyrrole and 11.2 parts of potassium carbonate are suspended in 80 parts of dimethylformamide, with stirring. The mixture is warmed to 142° C., a mixture of 11 parts of 1-bromobutane and 10 parts of dimethylformamide is added in the course of 50 minutes and the mixture is then subsequently stirred at 142° C. for 30 minutes. After cooling to 25° C., the reaction mixture is filtered, the precipitate is washed with 20 parts of dimethylformamide and the filtrate is evaporated under reduced pressure. Methanol is added to the still warm residue and the resulting suspension is cooled to 20° C. and filtered. The product obtained is washed with methanol and then with hot water at 90° C. and dried. 3.9 parts of a crude product which, after crystallisation from 80 parts of n-butanol, gives 3.3 parts of 1,4-diketo-2,5-di-n-butyl-3,6-di-(4'-chlorophenyl)-pyrrolo-[3,4-c]-pyrrole of the following formula in the form of orange-red crystals of melting point 176°–177° C., are obtained.

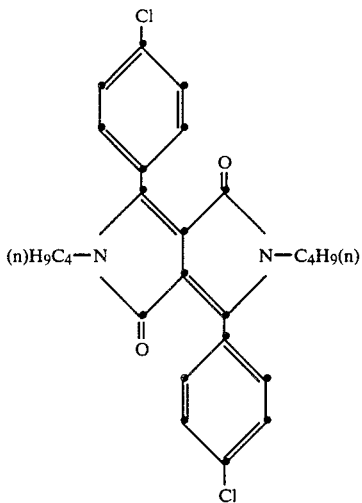

What is claimed is:

1. A colored composition, containing a polymer-soluble dye or pigment, which comprises
   (a) a high molecular weight organic material, and
   (b) an effective amount of a compound of formula I

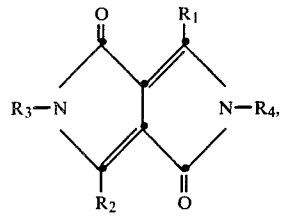

in which $R_1$ and $R_2$ are phenyl or said phenyl substituted by one or two fluorine, chlorine or bromine atoms or mixtures thereof, by one, two or three methyl or methoxy groups or mixtures thereof with chlorine atoms, by cyano, by dimethylamino, by trifluoromethyl, by tert-butyl, by hydroxy, by alkoxycarbonyl of 2 to 3 carbon atoms, by benzoylamino or by acetyl; naphthyl or said naphthyl substituted by methoxy; anthryl or phenanthryl; and $R_3$ and $R_4$ are both other than hydrogen and are $C_1$–$C_{12}$-alkyl, $C_2$–$C_{13}$-alkoxycarbonyl, carboethoxymethyl, cyanomethyl, benzoyl, benzyl, allyl, phenyl or said phenyl substituted by chlorine or by bromine, or the group of the formula

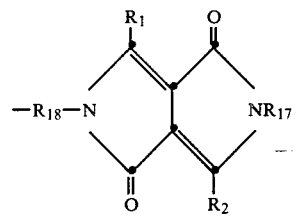

in which $R_1$ and $R_2$ are as defined above, $R_{17}$ is hydrogen and $R_{18}$ is a divalent radical derived from a $C_1$–$C_8$-dihaloalkane, $C_{1-10}$-dicarboxylic acid halide, phenylene dihalide or xylylene dihalide.

2. A composition according to claim 1 wherein component (a) is a polyester or polystyrene.

3. A composition according to claim 1 wherein component (b) is a compound of formula I wherein $R_1$ and $R_2$ are the same and each is phenyl, 4-chlorophenyl, 3-cyanophenyl, 4-cyanophenyl, 3-chlorophenyl, 3-methylphenyl or 4-methylphenyl, and $R_3$ and $R_4$ are the same and each is methyl, ethyl, n-butyl, allyl, 4-chlorophenyl, benzoyl, benzyl, ethoxycarbonylmethyl or cyanomethyl.

4. A composition according to claim 1 wherein component (b) is a compound of formula I wherein $R_1$ and $R_2$ are each phenyl, and $R_3$ and $R_4$ are each n-butyl.

5. A composition according to claim 1 wherein component (b) is a compound of formula I wherein $R_1$ and $R_2$ are each phenyl, and $R_3$ and $R_4$ are each methyl.

6. A composition according to claim 1 wherein component (b) is a compound of formula I wherein $R_1$ and $R_2$ are each phenyl, and $R_3$ and $R_4$ are each benzyl.

7. A colored composition, containing a polymer-soluble dye or pigment, which comprises
   (a) a high molecular weight organic material, and (b) an effective amount of a compound of formula I
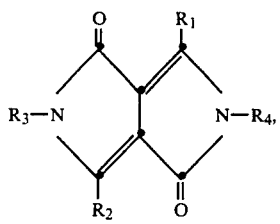 (I)
in which $R_1$ and $R_2$ are each phenyl, $R_3$ is hydrogen, and $R_4$ is cyanomethyl, n-butyl or the group of the formula
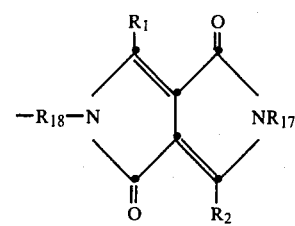
in which $R_1$ and $R_2$ are phenyl, $R_{17}$ is hydrogen, and $R_{18}$ is m-xylylene.
8. A composition according to claim 7 wherein component (a) is a polyester or polystyrene.